United States Patent [19]

Kasuga et al.

[11] Patent Number: 4,643,982

[45] Date of Patent: Feb. 17, 1987

[54] HIGH-STRENGTH GLASS-CERAMIC CONTAINING ANORTHITE CRYSTALS AND PROCESS FOR PRODUCING THE SAME

[75] Inventors: Toshihiro Kasuga, Akishimashi; Kenji Nakagawa, Tokorozawa, both of Japan

[73] Assignee: Hoya Corporation, Tokyo, Japan

[21] Appl. No.: 804,517

[22] Filed: Dec. 4, 1985

[30] Foreign Application Priority Data

Dec. 5, 1984 [JP] Japan .................................. 59-255848
Dec. 11, 1984 [JP] Japan .................................. 59-260037

[51] Int. Cl.$^4$ ...................... C03C 10/06; C03C 10/04; C03C 10/02

[52] U.S. Cl. ........................................ 501/8; 501/5; 501/10

[58] Field of Search .................................. 501/5, 8, 10

[56] References Cited

U.S. PATENT DOCUMENTS 4,358,541 11/1982 Andrus et al. .......................... 501/8
4,560,666 12/1985 Yoshida et al. ....................... 501/10

Primary Examiner—Mark L. Bell
Attorney, Agent, or Firm—Cushman, Darby & Cushman

[57] ABSTRACT

A high-strength glass-ceramic containing apatite crystals or $\beta$-tricalcium phosphate crystals, and anorthite crystals, and a process for producing the same are disclosed. The glass-ceramic has an excellent biocompatibility and is useful as an implant material such as an artificial dental root and an artificial bone.

5 Claims, 2 Drawing Figures

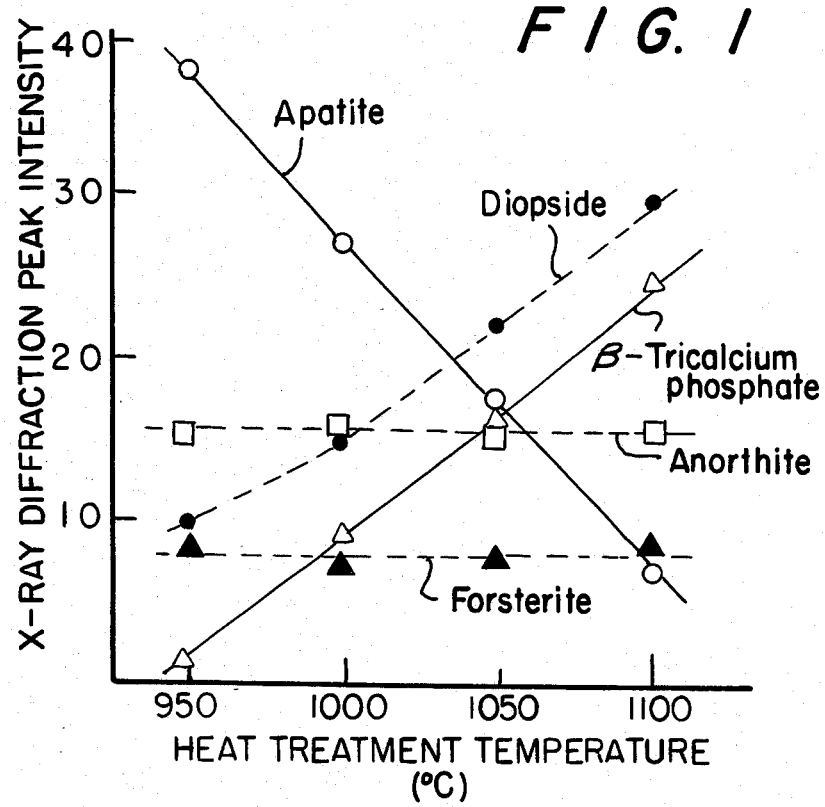
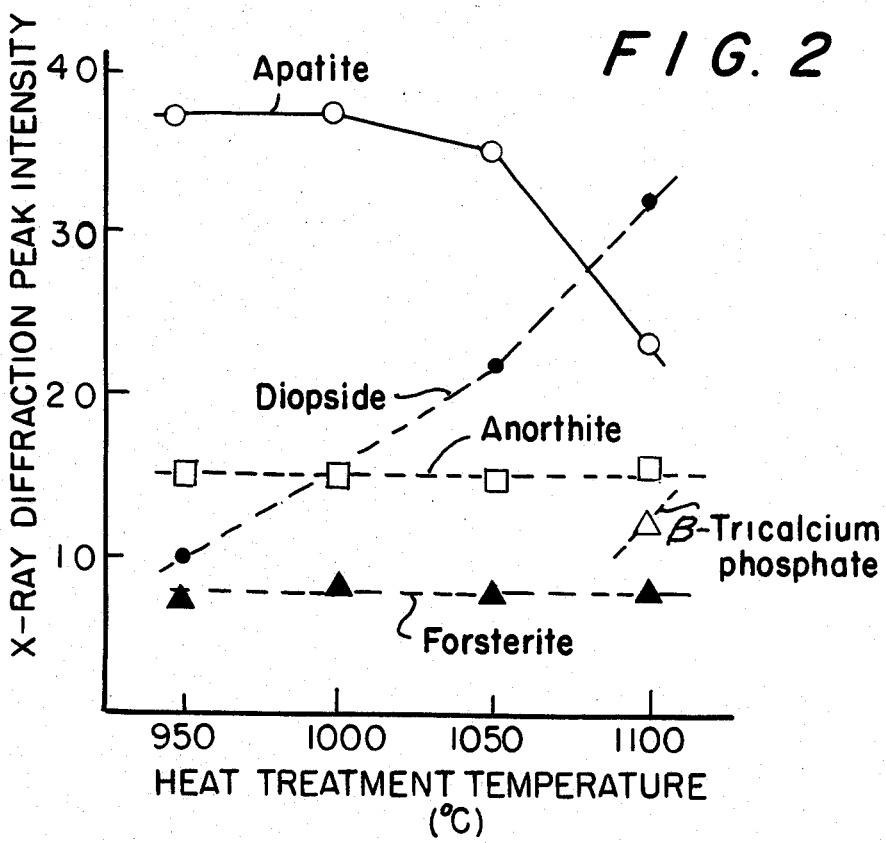

4,643,982

HIGH-STRENGTH GLASS-CERAMIC CONTAINING ANORTHITE CRYSTALS AND PROCESS FOR PRODUCING THE SAME

FIELD OF THE INVENTION

The present invention relates to a high-strength glass-ceramic useful as an implant material such as artificial dental roots or artificial bones. More particularly, the invention relates to a high-strength glass-ceramic containing anorthite crystals, and a process for producing the high-strength glass-ceramic.

BACKGROUND OF THE INVENTION

One of the conventional glass-ceramics useful as biomaterials is the glass-ceramic containing apatite crystals and wollastonite crystals. This glass-ceramic is prepared by the following procedure: grinding the $MgO-CaO-SiO_2-P_2O_5$ system glass with a MgO content of up to 7 wt % to 200 mesh or less powders; compression molding the resulting glass powders; heat-treating the molding in the sintering temperature range of the glass powders; and subsequently heat-treating the sintered glass powder molding in a temperature range where the apatite crystals $[Ca_{10}(PO_4)_6O]$ and the wollastonite crystals $[CaO.SiO_2]$ are formed. Further, a glass-ceramic obtained from the $MgO-CaO-SiO_2-P_2O_5$ system glass containing 8 wt % or more MgO is known. This glass-ceramic contains apatite crystals and alkaline earth metal silicate crystals such as diopside $[CaO.MgO.2SiO_2]$, forsterite $[2MgO.SiO_2]$ or akermanite $[2CaO.MgO.2SiO_2]$.

In these glass-ceramics, the apatite crystals contribute to their biocompatibility and the alkaline earth silicate crystals such as wollastonite, diopside, forsterite and akermanite contribute to the mechanical strength of the glass-ceramics. Therefore, in order to provide a glass-ceramic having not only good biocompatibility but also high mechanical strength, the contents of both apatite crystals and alkaline earth metal silicate crystals are desirably increased.

The conventional glass-ceramic useful as a biomaterial has a bending strength of about 1,200 to 1,400 kg/cm$^2$ in the glass-ceramic with a MgO content of up to 7 wt %, and about 1,500 to 1,800 kg/cm$^2$ in the glass-ceramic with a MgO content of 8 wt % or more. These values, however, are not completely satisfactory for the purpose of using such glass-ceramic as artificial dental roots or artificial bones.

It is known that tricalcium phosphate crystals are a component which is absorbed into a living body to derive bone formation. A material wherein a sintered product of the tricalcium phosphate is arranged on the surface of a polymethyl methacrylate is used as an artificial dental root, and a porous sintered product of the tricalcium phosphate crystal is used as a substitute for bone.

The tricalcium phosphate crystal has the characteristic that the crystal is absorbed in the living body to derive the bone formation as described above. However, due to this characteristic, where the sintered product of the crystal is actually used as the implant material, the material must be designed, taking into consideration the absorption rate into living body and the bone formation rate.

SUMMARY OF THE INVENTION

Accordingly, one object of the present invention is to provide a glass-ceramic containing apatite crystals and anorthite crystals which has good biocompatibility and also exhibits a greater strength than the conventional product, and a process for producing such glass-ceramic.

Another object of the present invention is to provide a glass-ceramic containing β-tricalcium phosphate crystals and anorthite crystals which is free from the disadvantages of the conventional product, and a process for producing such glass-ceramic.

BRIEF DESCRIPTION OF THE DRAWINGS

FIGS. 1 and 2 each is a graph showing the relationship between a heat treatment temperature of the glass-ceramic of the present invention and an X-ray diffraction intensity of crystals precipitated in the glass-ceramic.

DETAILED DESCRIPTION OF THE INVENTION

The glass-ceramic according to the present invention has a composition comprising, in % by weight
  8 to 26% MgO;
  18 to 43% CaO;
  25 to 40% SiO$_2$;
  10 to 25% P$_2$O$_5$;
  10 to 25% Al$_2$O$_3$;
  0 to 3% F$_2$;
  0 to 10% Li$_2$O;
  0 to 10% Na$_2$O;
  0 to 10% K$_2$O;
  0 to 10% B$_2$O$_3$;
  0 to 10% TiO$_2$;
  0 to 10% SrO;
  0 to 10% Nb$_2$O$_5$;
  0 to 10% Ta$_2$O$_5$; and
  0 to 10% of ZrO$_2$,
the total amounts of MgO, CaO, SiO$_2$, P$_2$O$_5$, Al$_2$O$_3$ and F$_2$ being at least 90%.

The glass-ceramic according to the first embodiment of the present invention contains both apatite crystals and anorthite crystals [CaO.Al$_2$O$_3$.2SiO$_2$] and has a composition comprising, in % by weight
  8 to 26% MgO;
  18 to 43% CaO;
  25 to 40% SiO$_2$;
  10 to 25% P$_2$O$_5$;
  10 to 25% Al$_2$O$_3$;
  0.5 to 3% F$_2$;
  0 to 10% Li$_2$O;
  0 to 10% Na$_2$O;
  0 to 10% K$_2$O;
  0 to 10% B$_2$O$_3$;
  0 to 10% TiO$_2$;
  0 to 10% SrO;
  0 to 10% Nb$_2$O$_5$;
  0 to 10% Ta$_2$O$_5$; and
  0 to 10% of ZrO$_2$,
the total amounts of MgO, CaO, SiO$_2$, P$_2$O$_5$, Al$_2$O$_3$ and F$_2$ being at least 90%.

The above glass-ceramic of the present invention may also contain one or more crystals selected from the group consisting of the alkaline earth metal silicate crystals such as diopside, forsterite and akermanite, and β-tricalcium phosphate crystals.

The glass-ceramic according to the first embodiment of the present invention described above can be produced by a process which comprises preparing 200 mesh or less glass powders having a composition comprising, in % by weight, 8 to 26% MgO; 18 to 43% CaO; 25 to 40% $SiO_2$; 10 to 25% $P_2O_5$; 10 to 25% $Al_2O_3$; 0.5 to 3% $F_2$; 0 to 10% $Li_2O$; 0 to 10% $Na_2O$; 0 to 10% $K_2O$; 0 to 10% $B_2O_3$; 0 to 10% $TiO_2$; 0 to 10% SrO: 0 to 10% $Nb_2O_5$; 0 to 10% $Ta_2O_5$ and 0 to 10% $ZrO_2$, the total amounts of MgO, CaO, $SiO_2$, $P_2O_5$, $Al_2O_3$ and $F_2$ being at least 90%;

molding the glass powders;

heat-treating the resulting molding in the sintering temperature range of the glass powders; and further heat-treating the molding in a temperature range where the apatite crystals and anorthite crystals are formed.

The reason why the amount of each component of the glass-ceramic according to the first embodiment of the present invention is limited to the above-specified range will hereinafter be explained.

If the amount of MgO is less than 8%, the sintering temperature range of the resulting glass composition is close to a crystal-forming temperature range. Therefore, crystallization occurs before disappearance of pores due to sintering and it is difficult to obtain a glass-ceramic of dense structure. On the other hand, if the amount of MgO is more than 26%, the amount of apatite crystals formed is undesirably small. Thus, the MgO content is limited to a range of from 8 to 26%.

If the amount of CaO is less than 18%, the amount of apatite crystals formed is undesirably small. On the other hand, if the amount of CaO is more than 43%, devitrification tendency of glass is markable and it is difficult to produce the desired glass-ceramic. Thus, the CaO content is limited to a range of from 18 to 43%.

If the amount of $SiO_2$ is less than 25%, devitrification of glass tends to occur and it is difficult to produce the desired glass-ceramic. Moreover, since the amounts of aluminum, calcium and magnesium silicate crystals formed are small, it is difficult to obtain a glass-ceramic having a high strength. On the other hand, if the amount of $SiO_2$ is more than 40%, the resulting glass tends to cause phase separation and a uniform glass cannot be obtained. Thus, the $SiO_2$ content is limited to a range of from 25 to 40%.

If the amount of $P_2O_5$ is less than 10%, the apatite crystals are formed only in small amounts. On the other hand, if the amount of $P_2O_5$ is more than 25%, the phase separation occurs and a uniform glass cannot be obtained. Thus, the $P_2O_5$ content is limited to a range of from 10 to 25%.

If the amount of $Al_2O_3$ is less than 10%, it is difficult to form the anorthite crystals and it is therefore difficult to provide the desired strength to the glass-ceramic. On the other hand, if the amount of $Al_2O_3$ is more than 25%, the amount of the apatite crystals formed is decreased. Therefore, the $Al_2O_3$ content is limited to a range of from 10 to 25%.

If the amount of $F_2$ is less than 0.5%, it is difficult to form the apatite crystals. On the other hand, if the amount of $F_2$ is more than 3%, devitrification of glass tends to occur. Therefore, the $F_2$ content is limited to a range of from 0.5 to 3%.

As described above, $F_2$ is the essential component to form the apatite crystals in the glass-ceramic of the present invention. The effects of $F_2$ on the formation of the apatite crystals are explained below.

Glasses: glass (A) having a composition comprising, in % by weight, 11.5% MgO; 27.0% CaO; 34.3% $SiO_2$; 14.2% $P_2O_5$; and 13.0% $Al_2O_3$; glass (B) having the same composition as that of (A) except that 0.5% of oxygen is replaced by fluorine; and glass powder (C) having the same composition as that of powder (A) except that 1.5% of oxygen is replaced by fluorine each is ground to a particle size of 200 mesh or less and compression molded. Each molding is placed in an electric furnace and heated from room temperature at a rate of 10° C./min. Each molding is maintained therein at a constant temperature in the range of 900° to 1,100° C. for 2 hours and cooled to room temperature to obtain glass-ceramic samples (A) to (C). These samples were ground into particles and the crystals in each sample are identified by powder X-ray diffraction. In sample (A) which does not contain fluorine, the β-tricalcium phosphate, anorthite, diopside and forsterite crystals are detected but apatite crystals are not observed. In contrast, samples (B) and (C) with the fluorine content of 0.5% and 1.5%, respectively, are found to contain apatite, β-tricalcium phosphate, anorthite, diopside and forsterite crystals. These results show that fluorine is the essential component to form the apatite crystals.

In the glass-ceramic according to the first embodiment of the present invention, the amounts of the apatite, β-tricalcium phosphate and diopside formed in the glass-ceramic depend on the fluorine content and the heat treatment temperature, and this relationship is shown in FIGS. 1 and 2.

FIG. 1 shows the relationship between the heat treatment temperature of sample (B) with 0.5% fluorine and the diffraction intensities for apatite crystal (d=2.18 A), β-tricalcium phosphate crystal (d=2.88 A), anorthite crystal (d=4.04 A), diopside crystal (d=2.99 A) and forsterite crystal (d=3.88 A). As is apparent from FIG. 1, the amounts of the diopside and β-tricalcium phosphate crystals formed increase and the amount of the apatite crystal formed decreases with increasing the heat treatment temperature (retention temperature).

FIG. 2 shows the same temperature vs. diffraction intensity profile as in FIG. 1 for sample (C) containing 1.5% fluorine. The amount of apatite crystal does not substantially change in the heat treatment temperature range of from about 950° to about 1,050° C., but at higher temperatures, the amount of the apatite crystal formed decreases and in place thereof, the β-tricalcium phosphate crystal forms. On the other hand, the amount of diopside crystal formed increases monotonously with increase of the heat treatment temperature.

A higher content of diopside crystal is desirable to provide the glass-ceramic with an enhanced mechanical strength, whereas a higher content of apatite crystal is desirable to increase the biocompatibility of the glass-ceramic.

A glass-ceramic having high contents of apatite and diopside crystals can be obtained by heat-treating a fluorine-containing glass composition at high temperatures. Thus, fluorine is an effective component to produce a glass-ceramic having high strength and good biocompatibility.

In addition to the six essential components described above, the glass-ceramic of the present invention can contain 10 wt % or less of at least one optional component selected from the group consisting of $Li_2O$, $Na_2O$, $K_2O$, SrO, $B_2O_3$, $TiO_2$, $Nb_2O_5$, $Al_2O_3$ and $ZrO_2$, which are harmless to a human body. If the total amount of these optional components exceeds 10 wt % of the glass-ceramic, the amounts of the apatite crystals and alkaline earth metal silicate crystals formed are reduced. Therefore, the total amount of the six essential components, MgO, CaO, $SiO_2$, $P_2O_5$, $Al_2O_3$ and $F_2$, must be at least 90 wt % of the glass-ceramic.

In producing the glass-ceramic according to the first embodiment of the present invention, it is essential that a parent glass having the compositional ranges defined above is ground into particles of 200 mesh or less, the resulting glass powder is molded into a desired shape, the molding is sintered, and the sintered product is subjected to a crystallization treatment. If the base glass is directly molded into the desired shape from a molten state without grinding and the molding is heat-treated, apatite crystals are uniformly dispersed and precipitated, but the anorthite and the alkaline earth metal silicate crystals such as diopside, akermanite and forsterite crystallize from the glass surface, causing internal cracking. As a result, a glass-ceramic with an enhanced strength cannot be obtained. Even if the base glass is ground, if the particle size is larger than 200 mesh, pores tend to remain in the glass-ceramic. In this case, a glass-ceramic having the desired high mechanical strength cannot be obtained. Therefore, in order to obtain a high-strength glass-ceramic containing less pores and having a uniform crystal distribution, it is important to use the parent glass fine powders having a particle diameter of 200 mesh or less.

In accordance with the process in the first embodiment of the present invention, the parent glass powder having a particle size of 200 mesh or less is first molded into a desired shape by any conventional technique, the shaped powder is heat-treated in the sintering temperature range of the glass powder, and the sintered glass powder is then heat-treated in a temperature range where the apatite crystal and the alkaline earth metal silicate crystals such as anorthite, diopside, akermanite and forsterite are formed. Heat treatment in the sintering temperature range of the glass powder is important to produce a pore-free glass-ceramic having a large mechanical strength.

The sintering temperature range of the glass powders can be determined by heating a molding of the glass powders at a constant temperature-raising speed and measuring a heat shrinkage of the molding due to the sintering thereof. The sintering temperature range is from a temperature at which the heat shrinkage starts to a temperature at which the heat shrinkage finishes.

A heat treatment within the apatite crystal-forming temperature range is important to precipitate a large amount of apatite crystals necessary for chemically bonding the resulting glass-ceramic to a bone. A heat treatment within the temperature range where anorthite and alkaline earth metal silicate crystals such as diopside, akermanite and forsterite are formed is important to precipitate a large amount of alkaline earth metal silicate crystals, thereby increasing the mechanical strength of the resulting glass-ceramic. Each crystal-forming temperature range can be determined by a differential thermal analysis of the glass powders. The glass powders are heat treated at a temperature at which an exothermic peak appears in a differential thermal analytical curve and then is subjected to an X-ray diffraction analysis. By analyzing the data of X-ray diffraction analysis, precipitated crystals corresponding to the exothermic peak are identified. The crystal-forming temperature range for each crystal is from a temperature at which exothermic peak starts to a temperature at which exothermic peak finishes. In general, the each crystal-forming temperature range is from 1,000° to 1,150° C.

The glass-ceramic according to the second embodiment of the present invention contains at least one crystal selected from diopside, forsterite and akermanite, $\beta$-tricalcium phosphate crystal [$\beta$-$Ca_3(PO_4)_2$], and anorthite crystal, and has a composition comprising, in % by weight, 8 to 26% MgO;
18 to 43% CaO;
25 to 40% $SiO_2$;
10 to 25% $P_2O_5$;
10 to 25% $Al_2O_3$;
0 to 10% $Li_2O$;
0 to 10% $Na_2O$;
0 to 10% $K_2O$;
0 to 10% $B_2O_3$;
0 to 10% $TiO_2$;
0 to 10% $ZrO_2$;
0 to 10% SrO;
0 to 10% $Nb_2O_5$; and
0 to 10% $Ta_2O_5$, the total amonts of MgO, CaO, $SiO_2$, $P_2O_5$ and $Al_2O_3$ being at least 90%.

The glass-ceramic according to the second embodiment of the present invention described above can be produced by a process which comprises preparing 200 mesh or less glass powders having composition comprising, in % by weight, 8 to 26% MgO; 18 to 43% CaO; 25 to 40% $SiO_2$; 10 to 25% of $P_2O_5$; 10 to 25% $Al_2O_3$; 0 to 10% $Li_2O$; 0 to 10% $Na_2O$, 0 to 10% $K_2O$; 0 to 10% $B_2O_3$, 0 to 10% $TiO_2$; 0 to 10% of $ZrO_2$; 0 to 10% SrO, 0 to 10% $Nb_2O_5$; and 0 to 10% $Ta_2O_5$, the total amounts of MgO, CaO, $SiO_2$, $P_2O_5$ and $Al_2O_3$ being at least 90%;

molding the glass powders;

heat-treating the resulting molding in the sintering temperature range of the glass powder; and further heat-treating the molding in a temperature range where the $\beta$-tricalcium phosphate crystals and anorthite crystals are formed. In this case, by the heat-treatment in both crystals-forming temperature range, at least one crystal of diopside, forsterite and akermanite precipitates in the glass-ceramic according to the second embodiment of the present invention.

The reason why the amount of each component of the glass-ceramic according to the second embodiment of the present invention is limited to the above-specified range will hereinafter be explained.

If the amount of MgO is less than 8%, the sintering temperature range of the resulting glass composition is close to a crystal-forming temperature range. Therefore, crystallization occurs before disappearance of pores due to sintering and it is difficult to obtain a glass-ceramic of dense structure. On the other hand, if the amount of MgO is more than 26%, the amount of $\beta$-tricalcium phosphate crystals formed is undesirably small. Thus, the MgO content is limited to a range of from 8 to 26%.

If the amount of CaO is less than 18%, the amount of $\beta$-tricalcium phosphate crystals formed is undesirably small. On the other hand, if the amount of CaO is more than 43%, devitrification tendency of glass is markable and it is difficult to produce the desired glass-ceramic. Thus, the CaO content is limited to a range of from 18 to 43%.

If the amount of SiO$_2$ is less than 25%, devitrification of glass tends to occur and it is difficult to produce the desired glass-ceramic. Moreover, since the amounts of aluminum, calcium and magnesium (alkaline earth metals) silicate crystals formed are small, it is difficult to obtain a glass-ceramic having a high strength. On the other hand, if the amount of SiO$_2$ is more than 40%, the resulting glass tends to cause phase separation and a uniform glass cannot be obtained. Thus, the SiO$_2$ content is limited to a range of from 25 to 40%.

If the amount of P$_2$O$_5$ is less than 10%, the apatite crystals which are a precursor of α-tricalcium phosphate crystals are formed only in small amounts. On the other hand, if the amount of P$_2$O$_5$ is more than 25%, the phase separation occurs and a uniform glass cannot be obtained. Thus, the P$_2$O$_5$ content is limited to a range of from 10 to 25%.

If the amount of Al$_2$O$_3$ is less than 10%, it is difficult to form anorthite crystals and it is therefore difficult to provide the desired strength to the glass-ceramic. On the other hand, if the amount of Al$_2$O$_3$ is more than 25%, the amount of the β-tricalcium phosphate crystals formed is reduced. Therefore, the Al$_2$O$_3$ content is limited to a range of from 10 to 25%.

The glass-ceramic of the present invention can contain, as well as the above-described five components, one or more of compounds selected from the group consisting of Li$_2$O, Na$_2$O, K$_2$O, SrO, B$_2$O$_3$, TiO$_2$, Nb$_2$O$_5$, Ta$_2$O$_5$ and ZrO$_2$, which are harmless to a human body, in a total amount of 10% or less. If the total amount of these additives is 10%, the amounts of β-tricalcium phosphate crystals and alkaline earth metal silicate crystals formed are reduced. Thus, the total amount of the additives is limited to 10% or less. Accordingly, the total amount of MgO, CaO, SiO$_2$, P$_2$O$_5$ and Al$_2$O$_3$ is limited to at least 90%.

The glass-ceramic according to the second embodiment of the present invention is produced in the following manner.

A glass having the above composition is ground to a particle size of 200 mesh or less and then molded into a desired form, followed by crystallization treatment. If, on the other hand, the glass is molded into the desired form directly from a moleten state and then heat treated, anorthite and alkaline earth metal silicate crystals such as diopside, akermanite and forsterite, precipitate from the glass surface, forming cracks in the inside of the glass-ceramic. As a result, a glass-ceramic having a high strength cannot be obtained.

Further, even if the glass is ground, if the particle size of the glass powder is more than 200 mesh, pores tend to remain in the glass-ceramic and a glass-ceramic having a large mechanical strength cannot be obtained. That is, in order to obtain a high strength glass-ceramic containing less pores and wherein fine particles of β-tricalcium phosphate crystals and silicate crystals such as anorthite, diopside, forsterite and akermanite are uniformly precipitated, it is important to employ glass fine powders having a particle size of 200 mesh or less.

In accordance with the process in the second embodiment of the present invention, the glass powder having a particle size of 200 mesh or less is molded into a desired shape by any conventional technique, the molding is heat-treated in the sintering temperature range of the glass powder, and the sintered product is further heat-treated in a temperature range where β-tricalcium phosphate crystals, anorthite and alkaline earth metal silicate crystals are formed. The heat-treatment in the sintering temperature range of the glass powder is important to obtain pore-free glass-ceramic having a large mechanical strength.

The sintering temperature range of the glass powders can be determined by heating a molding of the glass powders at a constant temperature-raising speed and measuring a heat shrinkage of the molding due to the sintering thereof. The sintering temperature range is from a temperature at which the heat shrinkage starts to a temperature at which the heat shrinkage finishes.

A heat treatment within the β-tricalcium phosphate crystal-forming temperature range is important to form a large amount of β-tricalcium phosphate crystals having the action of forming bones. A heat treatment within the temperature range where anorthite and alkaline earth metal silicate crystals such as diopside, akermanite and forsterite are formed is important to precipitate a large amount of those alkaline earth metal silicate crystals, thereby increasing the mechanical strength of the resulting glass-ceramic. Each crystal-forming temperature range can be determined by a differential thermal analysis of the glass powders. A glass powders are heat treated at a temperature at which an exothermic peak appears in a differential thermal analytical curve and then is subjected to an X-ray diffraction analysis. By analyzing the data of the X-ray diffraction analysis, precipitated crystals corresponding to the exothermic peak are identified. The crystal-forming temperature range for each crystal is from a temperature at which exothermic peak starts to a temperature at which exothermic peak finishes. In general, each crystal-forming temperature range is from 1,000° to 1,100° C.

The present invention is described in greater detail by reference to the following examples. Compositions are expressed in % by weight.

EXAMPLES

Glass compositions as shown in the Tables 1 and 2 below were prepared using oxides, carbonates, phosphates, hydrates and the like. Each glass composition was placed in a platinum crucible and melted at 1,400° to 1,500° C. for 30 to 60 minutes. The thus-obtained glass was quenched by pouring it into water in the molten state and dried. It was then placed in a pot mill and pulverized to a size of 350 mesh or less. A mixture of the glass powders and 5 wt % of paraffin as a binder was placed in a metallic mold and press-molded into a desired form under a pressure of 500 kg/cm$^2$.

The molding thus obtained was placed in an electric furnace, and heated from room temperature to a prescribed temperature between 1,050° and 1,150° C. at a constant temperature-rising rate of 3° C./min. and maintained at that temperature for 2 hours to achieve sintering and crystallization. Then, the molding was gradually cooled to room temperature in the furnace.

The glass-ceramic was ruptured, and the rupture cross-section was examined by SEM. It was found that the glass-ceramic had a dense structure that substantially no pore could be found. The glass sample was pulverized, and precipitated crystals were identified by X-ray diffraction analysis.

The results obtained and the glass compositions are shown in Tables 1 and 2 below.

Some samples were measured for a bending strength by using a rod having a diameter of about 5 mm the surface of which was polished with No. 300 diamond whetstone. The results are also shown in Tables 1 and 2 below.

TABLE 1

| Glass Composition | Example No. 1 | 2 | 3 | 4 | 5 | 6 | 7 |
|---|---|---|---|---|---|---|---|
| MgO | 13.3 | 11.5 | 11.5 | 9.4 | 10.2 | 9.1 | 13.3 |
| CaO | 28.9 | 26.7 | 26.8 | 17.8 | 23.6 | 33.2 | 33.2 |
| $Al_2O_3$ | 10.1 | 12.6 | 12.7 | 23.8 | 16.9 | 11.6 | 11.6 |
| $SiO_2$ | 33.0 | 34.0 | 34.1 | 34.0 | 33.8 | 29.0 | 24.8 |
| $P_2O_5$ | 13.7 | 14.0 | 14.1 | 14.0 | 14.0 | 16.1 | 16.1 |
| $F_2$ | 1.0 | 1.2 | 0.8 | 1.0 | 1.5 | 1.0 | 1.0 |
| Additives | — | — | — | — | — | — | — |
| Retention Temperature (°C.) | 1000 | 1050 | 1150 | 1100 | 1100 | 1050 | 1000 |
| Type of Crystals Precipitated | Apatite Anorthite Diopside Forsterite | Apatite Anorthite Diopside Forsterite | Apatite Anorthite Diopside Forsterite β-Tricalcium phosphate | Apatite Anorthite Diopside | Apatite Anorthite Diopside Forsterite | Apatite Anorthite Akermanite Diopside | Apatite Anorthite Akermanite Diopside |
| Bending Strength (kg/cm²) | 2100 | 1700 | 2300 | — | 1800 | 2000 | — |

| Glass Composition | Example No. 8 | 9 | 10 | 11 | 12 | 13 |
|---|---|---|---|---|---|---|
| MgO | 9.1 | 10.5 | 11.8 | 10.9 | 10.9 | 10.9 |
| CaO | 24.9 | 24.6 | 27.6 | 25.5 | 25.5 | 25.5 |
| $Al_2O_3$ | 11.6 | 11.7 | 13.6 | 12.6 | 12.6 | 12.6 |
| $SiO_2$ | 37.3 | 31.2 | 35.0 | 32.5 | 32.5 | 32.5 |
| $P_2O_5$ | 16.1 | 21.0 | 11.4 | 13.5 | 13.5 | 13.5 |
| $F_2$ | 1.0 | 1.0 | 1.0 | 1.0 | 1.0 | 1.0 |
| Additives | — | — | — | $Li_2O$ 4.0 | $B_2O_3$ 4.0 | $TiO_2$ 4.0 |
| Retention Temperature (°C.) | 1000 | 1050 | 1000 | 1000 | 1000 | 1050 |
| Type of Crystals Precipitated | Apatite Anorthite Diopside | Apatite Anorthite Diopside Forsterite β-Tricalcium phosphate | Apatite Anorthite Diopside Forsterite | Apatite Anorthite Diopside Forsterite | Apatite Anorthite Diopside Forsterite | Apatite Anorthite Diopside Forsterite |
| Bending Strength (kg/cm²) | 1700 | 1900 | — | — | — | 2000 |

| Glass Composition | Example No. 14 | 15 | 16 | 17 |
|---|---|---|---|---|
| MgO | 10.9 | 10.9 | 10.9 | 10.9 |
| CaO | 25.5 | 25.5 | 25.5 | 25.5 |
| $Al_2O_3$ | 12.6 | 12.6 | 12.6 | 12.6 |
| $SiO_2$ | 32.5 | 32.5 | 32.5 | 32.5 |
| $P_2O_5$ | 13.5 | 13.5 | 13.5 | 13.5 |
| $F_2$ | 1.0 | 1.0 | 1.0 | 1.0 |
| Additives | SrO 4.0 | $Nb_2O_5$ 4.0 | $Ta_2O_5$ 4.0 | $ZrO_2$ 4.0 |
| Retention Temperature (°C.) | 1000 | 1050 | 1050 | 1050 |
| Type of Crystals Precipitated | Apatite Anorthite Diopside Forsterite | Apatite Anorthite Diopside Forsterite | Apatite Anorthite Diopside Forsterite | Apatite Anorthite Diopside Forsterite |
| Bending Strength (kg/cm²) | — | — | 2100 | 2000 |

TABLE 2

| Glass Composition | Example No. 18 | 19 | 20 | 21 | 22 |
|---|---|---|---|---|---|
| MgO | 13.8 | 11.6 | 9.0 | 8.7 | 10.3 |
| CaO | 30.0 | 27.0 | 21.0 | 18.0 | 24.0 |
| $Al_2O_3$ | 10.5 | 12.8 | 21.4 | 24.7 | 17.2 |
| $SiO_2$ | 34.3 | 34.4 | 34.4 | 34.4 | 34.3 |
| $P_2O_5$ | 14.2 | 14.2 | 14.2 | 14.2 | 14.2 |
| Additives | | | | | |
| Retention Temperature (°C.) | 1100 | 1100 | 1050 | 1050 | 1050 |
| Type of Crystals Precipitated | β-Tricalcium phosphate Anorthite Diopside | β-Tricalcium phosphate Anorthite Diopside | β-Tricalcium phosphate Anorthite Diopside | β-Tricalcium phosphate Anorthite Diopside | β-Tricalcium phosphate Anorthite Diopside |

TABLE 2-continued

|  | Forsterite | Forsterite |  |  | Forsterite |
|---|---|---|---|---|---|
| Bending Strength (kg/cm²) | 2200 | 2300 | — | — | 1700 |

| | Example No. | | | | |
|---|---|---|---|---|---|
| | 23 | 24 | 25 | 26 | 27 |
| Glass Composition | | | | | |
| MgO | 13.4 | 10.6 | 11.9 | 11.0 | 11.0 |
| CaO | 33.5 | 25.0 | 27.9 | 25.7 | 25.7 |
| Al$_2$O$_3$ | 11.7 | 11.6 | 13.3 | 12.5 | 12.5 |
| SiO$_2$ | 25.1 | 31.5 | 35.4 | 32.8 | 32.8 |
| P$_2$O$_5$ | 16.3 | 21.3 | 11.5 | 14.0 | 14.0 |
| Additives | | | | Na$_2$O 4.0 | B$_2$O$_3$ 4.0 |
| Retention Temperature (°C.) | 1100 | 1100 | 1000 | 1000 | 1000 |
| Type of Crystals Precipitated | β-Tricalcium phosphate Anorthite Akermanite Diopside | β-Tricalcium phosphate Anorthite Diopside Forsterite | β-Tricalcium phosphate Anorthite Diopside Forsterite | β-Tricalcium phosphate Anorthite Diopside Forsterite | β-Tricalcium phosphate Anorthite Diopside Forsterite |
| Bending Strength (kg/cm²) | 2000 | 1900 | — | — | — |

| | Example No. | | | | |
|---|---|---|---|---|---|
| | 28 | 29 | 30 | 31 | 32 |
| Glass Composition | | | | | |
| MgO | 11.0 | 11.0 | 11.0 | 11.0 | 11.0 |
| CaO | 25.7 | 25.7 | 25.7 | 25.7 | 25.7 |
| Al$_2$O$_3$ | 12.5 | 12.5 | 12.5 | 12.5 | 12.5 |
| SiO$_2$ | 32.8 | 32.8 | 32.8 | 32.8 | 32.8 |
| P$_2$O$_5$ | 14.0 | 14.0 | 14.0 | 14.0 | 14.0 |
| Additives | TiO$_2$ 4.0 | SrO 4.0 | Nb$_2$O$_5$ 4.0 | Ta$_2$O$_5$ 4.0 | ZrO$_2$ 4.0 |
| Retention Temperature (°C.) | 1100 | 1000 | 1000 | 1100 | 1100 |
| Type of Crystals Precipitated | β-Tricalcium phosphate Anorthite Diopside Forsterite | β-Tricalcium phosphate Anorthite Diopside Forsterite | β-Tricalcium phosphate Anorthite Diopside Forsterite | β-Tricalcium phosphate Anorthite Diopside Forsterite | β-Tricalcium phosphate Anorthite Diopside Forsterite |
| Bending Strength (kg/cm²) | 2200 | — | — | 2300 | 2200 |

As shown in Table 1 above, the glass-ceramic according to the first embodiment of the present invention contains a large amount of apatite crystals necessary for chemically bonding to a bone, and has a very high bending strength of from 1,700 to 2,300 kg/cm². In addition, the bending strength of the glass-ceramic does not substantially vary by the production lot, and as a result, the glass-ceramic is extremely useful as biomaterials for artificial bones, artificial dental roots and the like.

Further, as shown in Table 2 above, the glass-ceramic according to the second embodiment of the present invention contains a large amount of β-tricalcium phosphate crystals which derive the formation of bones. Therefore, the glass-ceramic is extremely useful as biomaterials for artificial bones, artificial dental roots and the like.

While the invention has been described in detail and with reference to specific embodiments thereof, it will be apparent to one skilled in the art that various changes and modifications can be made therein without departing from the spirit and scope thereof.

What is claimed is:

1. A high-strength glass-ceramic having a composition consisting essentially of anorthite crystals and consisting essentially of, in % by weight,
   8 to 26% MgO;
   18 to 43% CaO;
   25 to 40% SiO$_2$;
   10 to 25% P$_2$O$_5$;
   10.1 to 25% Al$_2$O$_3$;
   0 to 3% F$_2$;
   0 to 10% Li$_2$O;
   0 to 10% Na$_2$O;
   0 to 10% K$_2$O;
   0 to 10% B$_2$O$_3$;
   0 to 10% TiO$_2$;
   0 to 10% SrO;
   0 to 10% Nb$_2$O$_5$;
   0 to 10% Ta$_2$O$_5$; and
   0 to 10% ZrO$_2$;
   the total amounts of MgO, CaO, SiO$_2$, P$_2$O$_5$, Al$_2$O$_3$ and F$_2$ being at least 90%.

2. A high-strength glass-ceramic consisting essentially of apatite crystals and anorthite crystals, and having a composition consisting essentially of, in % by weight,
   8 to 26% MgO;
   18 to 43% CaO;
   25 to 40% SiO$_2$;
   10 to 25% P$_2$O$_5$;
   10.1 to 25% Al$_2$O$_3$;
   0.5 to 3% F$_2$;
   0 to 10% Li$_2$O;
   0 to 10% Na$_2$O;
   0 to 10% K$_2$O;
   0 to 10% B$_2$O$_3$;
   0 to 10% TiO$_2$;
   0 to 10% SrO;
   0 to 10% Nb$_2$O$_5$;
   0 to 10% Ta$_2$O$_5$; and
   0 to 10% ZrO$_2$;

the total amount of MgO, CaO, SiO$_2$, P$_2$O$_5$, Al$_2$O$_3$ and F$_2$ being at least 90%.

3. The high-strength glass-ceramic as in claim 2, further containing one or more crystals selected from the group consisting of the alkaline earth metal silicate crystals and β-tricalcium phosphate crystals.

4. The high-strength glass-ceramic as in claim 3, wherein the alkaline earth metal silicate crystals are selected from the group consisting of diopside, forsterite, akermanite and mixtures thereof, and β-tricalcium phosphate crystals.

5. A high-strength glass-ceramic consisting essentially of β-tricalcium phosphate crystals, anorthite crystals and crystals of at least one from the group consisting of diopside, forsterite and akermanite and having a composition consisting essentially of, in % by weight, 8 to 26% MgO;
18 to 43% CaO;
25 to 40% SiO$_2$;
10 to 25% P$_2$O$_5$;
10.1 to 25% Al$_2$O$_3$;
0 to 10% Li$_2$O;
0 to 10% Na$_2$O;
0 to 10% K$_2$O;
0 to 10% B$_2$O$_3$;
0 to 10% TiO$_2$;
0 to 10% ZrO$_2$;
0 to 10% SrO;
0 to 10% Nb$_2$O$_5$; and
0 to 10% Ta$_2$O$_5$,
the total amounts of MgO, CaO, SiO$_2$, P$_2$O$_5$ and Al$_2$O$_3$ being at least 90%.

* * * * *